(12) United States Patent
Ashikari et al.

(10) Patent No.: US 6,723,562 B1
(45) Date of Patent: Apr. 20, 2004

(54) DNA CONSTRUCT FOR TRANSFORMING A YEAST

(75) Inventors: Toshihiko Ashikari, Takatsuki (JP); Misa Ochiai, Mishima-gun (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/869,185

(22) PCT Filed: Oct. 26, 2000

(86) PCT No.: PCT/JP00/07491

§ 371 (c)(1),
(2), (4) Date: Jun. 25, 2001

(87) PCT Pub. No.: WO01/31000

PCT Pub. Date: May 3, 2001

(30) Foreign Application Priority Data

Oct. 26, 1999 (JP) .......................................... 11-304185

(51) Int. Cl.⁷ .............................. C12N 15/64
(52) U.S. Cl. .................... 435/477; 435/483; 435/320.1; 536/23.1
(58) Field of Search ................ 435/477, 483, 435/320.1, 471, 476; 536/23.1

(56) References Cited

U.S. PATENT DOCUMENTS 5,965,444 A * 10/1999 Ashikari et al.

FOREIGN PATENT DOCUMENTS

EP 0 699 748 A2 * 3/1996
EP 0 814 165 A2 * 12/1997

OTHER PUBLICATIONS

Kawahata et al (1999) Yeast 15:1–10.*
Storici et al., A 2–micron DNA–based marker recycling system for multiple gene disruption in the yeast *Saccharomyces cerevisiae,* Yeast, 15(4) Mar. 1999, pp 271–283.
Kawahata, M., A positive selection for plasmid loss in *Saccharomyces cerevisiae* using galactose–inducible growth inhibitory sequences, Yeast, 15(1), Jan. 1999 pp1–10.

* cited by examiner

*Primary Examiner*—James Ketter
(74) *Attorney, Agent, or Firm*—Paul E. White, Jr.; Manelli Denison & Selter PLLC

(57) ABSTRACT

A DNA construct comprising:
(1) a selective marker gene,
(2) a galactose-inducible growth inhibition sequence,
(3) a pair of FRT sequences in the same orientation flanking (1) and (2), and
(4) a DNA fragment capable of recombining with a yeast chromosomal DNA located at each end of (3), wherein said FRT sequences contain the following sequence: 5'-GAAGTTCCTATAC TTTCTAGA GAATAGGAACTTC-3' (SEQ ID NO: 1)

| inverted repeat (1) | spacer sequence | inverted repeat (2) | or a sequence substantially identical to said sequence.

9 Claims, 8 Drawing Sheets

FIG. 3

| | | |
|---|---|---|
| FRT | 5'-GAAGTTCCTATAC TTTCTAGA GAATAGGAACTTC-3' | (SEQ ID NO: 1) |
| | | |
| FRT2 | 5'-GAAGTTCCTATAC TTTCTAGA GAATAGGAAC-3' | (SEQ ID NO: 2) |
| FRT102 | 5'- GTTCCTATAC TTTCTAGA GAATAGGAACTTC-3' | (SEQ ID NO: 3) |
| | ↓ Recombination | |
| FRT2W | 5'-GTTCCTATAC TTTCTAGA GAATAGGAAC-3' | (SEQ ID NO: 4) |
| | | |
| FRT3 | 5'-GAAGTTCCTATAC TTTCTAGA GAATAGGA-3' | (SEQ ID NO: 5) |
| FRT103 | 5'-TTCCTATAC TTTCTAGA GAATAGGAACTTC-3' | (SEQ ID NO: 6) |
| | ↓ Recombination | |
| FRT3W | 5'-TTCCTATAC TTTCTAGA GAATAGGA-3' | (SEQ ID NO: 7) |
| | | |
| FRT4 | 5'-GAAGTTCCTATAC TTTCTAGA GAATAG-3' | (SEQ ID NO: 8) |
| FRT104 | 5'-CTATAC TTTCTAGA GAATAGGAACTTC-3' | (SEQ ID NO: 9) |
| | ↓ Recombination | |
| FRT4W | 5'-CTATAC TTTCTAGA GAATAG-3' | (SEQ ID NO: 10) | ns application PCT/JP00/07491 filed Oct. 26, 2000 which designated the U.S.

FIELD OF THE INVENTION

The present invention relates to a method for preparing a transformant lacking a selective marker gene using site-specific recombination of yeast. After a gene of interest is transferred into yeast by using this method, a transformant of yeast deprived of a selective marker gene and transfected with a desired character can be obtained. Yeasts obtained by transformation methods of the present invention can be used to produce liquors or bread based on yeasts of the genus Saccharomyces, and are especially useful in producing beer.

PRIOR ART

Although many gene transfer methods concerning yeasts have been reported, all of these methods require a selective marker for selecting a transformant because of low gene transfer efficiency. Selective markers include those restoring auxotrophy, but typically consist of resistance genes to drugs such as antibiotics because auxotrophy is often difficult to confer to yeasts. However, it would be desirable to remove and reuse selective marker genes to repeatedly transform the same strain because few classes of drug resistance genes can be efficiently used in yeast. It would be also desirable to remove selective marker genes from transformants from the aspect of safety in commercialization of recombinants.

In order to solve these problems, methods for removing selective marker genes from transformants have been developed. An example of these methods uses site-specific recombination.

Site-specific recombination occurs when a recombinase acts on two recognition sequences consisting of specific nucleotide sequences recognized by said recombinase to induce recombination between said recognition sequences. These recombinations invite such events as deletion, insertion or inversion according to the arrangement of a pair of recognition sequences. Four site-specific recombinations are known, ie, Cre/lox derived from bacteriophage P1, FLP/FRT derived from *Saccharomyces cerevisiae*, R/RS derived from *Zygosaccharomyces rouxii* and Gin/gix derived from bacteriophage Mu (each designated by the combination of a recombinase and the specific nucleotide sequence recognized by the recombinase).

*Saccharomyces cerevisiae* is known to have a cyclic double-stranded DNA called the 2 μm plasmid in the cells, and the presence of a site-specific recombination mechanism in the 2 μm plasmid has been shown (Broach, J. R., Guarascio, V. R. and Jayaram, M., Cell, 29, 227–234, 1982). The 2 μm plasmid is a cyclic plasmid of 6318 bp, which is known to have a pair of inverted repeats of 599 bp in its molecule and to undergo site-specific recombination between these inverted repeats. The recombination site between these inverted repeats contains a spacer sequence of 8 bp flanked by short inverted repeats of 13 bp containing one mismatch (FRT sequences) and followed by another 13-bp inverted repeat at one end. Site-specific recombination occurs when a recombinase (Flp protein) expressed by the FLP gene encoded by the plasmid itself acts on the FRT sequences consisting of a specific nucleotide sequence present in the recombination site in the inverted repeats.

A known FRT sequence is a 34-bp sequence consisting of a spacer sequence of 8 bp and inverted repeats of 13 bp (J. F. Senecoff, R. C. Bruckner, and M. M. Cox, Proc. Natl. Acad. Sci. USA, 82, 7270–7274, 1985). However, this 34-bp FRT sequence is not suitable for commercial use because site-specific recombination using this sequence leaves recognition sequences of the recombinase on chromosomes after recombination so that undesired recombination may be induced.

Thus, there was a need for suppressing recombination between recognition sequences left on chromosomes after recombination.

Some groups reported excision of selective marker genes using site-specific recombination with a recombinase and the recognition sequences of the recombinase, such as excision of selective marker genes using the FLP/FRT system in *Saccharomyces cerevisiae* (F. Storici, M. Coglievina and C. V. Bruschi, Yeast, 15, 271–283, 1999). Storici et al. used the kanMX4 gene or URA3K1 gene as a selective marker gene to transform *Saccharomyces cerevisiae* by integrating the selective marker gene between FRT sequences recurring in the same orientation in the case of Cir$^+$ strains carrying the 2 μm plasmid or integrating the selective marker gene together with the FLP gene between similar FRT sequences in the case of Cir$^0$ strains lacking the 2 μm plasmid. The resulting transformant was cultured in a non-selective medium to induce recombination between FRT sequences so that the selective marker gene was successfully removed. Taking advantage of the fact that a nucleotide change in the core (a 8-bp spacer sequence) of an FRT sequence induces recombination with a sequence having the same nucleotide change but suppresses recombination with a sequence having another nucleotide change, they suppressed undesired recombination between FRT a sequences left on chromosomes by using an FRT sequence having a different nucleotide change at each run of repeated transformation and excision of a selective marker gene. However, the selective marker gene excision efficiency of their method is as low as 0.01%–1.39% and thus it is not easy to select strains deprived of selective marker genes. Moreover, the number of nucleotide changes at the core of a FRT sequence is limited.

A method using the Zygosaccharomyces rouxii-derived site-specific recombination system R/RS in *Saccharomyces cerevisiae* was also developed (JPA 66587/98). According to this document, a selective marker gene and the R gene linked to a galactose-inducible promoter were integrated between RS sequences recurring in the same orientation to transform *Saccharomyces cerevisiae*. Several nucleotides were deleted from the outside of each of a pair of RS sequences flanking the R gene and the selective marker gene to suppress undesired recombination with RS sequences left after recombination. However, this method involved introducing a foreign gene for recombinase (R gene). Moreover, the excision efficiency of the selective marker gene varies with the strain of yeast to be transformed, and it is not easy to select strains deprived of a selective marker gene especially in commercial strains such as brewer's yeasts and wild-type yeasts due to the low excision efficiency of the selective marker gene.

A sequence which inhibits growth of cells when it is highly expressed in *Saccharomyces cerevisiae* (growth inhibition sequence) has been reported. Excision of selective marker genes with such a sequence has already been reported (M. Kawahata et al., Yeast 15, 1–10, 1999). Kawahata et al. inserted the URA3 gene and a growth inhibition sequence linked to a galactose-inducible promoter between the *E. coli*-derived hisG sequences of about 1.2 kb recurring in the same orientation and used this construct for transformation. They inserted the construct into a chromosome and then cultured it in a medium containing galactose to successfully remove the selective marker gene at an efficiency of 96% or more. However, this method is not suitable for commercial use because the selective marker gene is excised by homologous recombination to leave an unnecessary long sequence as an excision mark of the selective gene on the chromosome.

Accordingly, it is an object of the present invention to provide a method for preparing a transformant lacking a selective marker gene and efficiently expressing a desired gene of interest. It is also an object of the present invention to apply thus prepared transformant yeast to the production of liquors or bread, and especially beer.

DISCLOSURE OF THE INVENTION

We found a method for preparing a yeast transformant lacking a selective marker gene by combining FRT sequences and a growth inhibition sequence in order to solve the above problems.

Specifically, the present invention provides a DNA construct comprising:
(1) a selective marker gene,
(2) a galactose-inducible growth inhibition sequence,
(3) a pair of FRT sequences in the same orientation flanking (1) and (2), and
(4) a DNA fragment capable of recombining with a yeast chromosomal DNA located at each end of (3),
wherein said FRT sequences contain the following sequence: 5'-<u>GAAGTTCCTATAC</u> TTTCTAGA <u>CAATAGGACTTC</u>-3' (SEQ ID NO: 1)
  inverted     spacer      inverted
  repeat (1)   sequence    repeat (1)
or a sequence substantially identical to said sequence, provided that in each member of said pair of FRT sequences, the inverted repeat distal from the flanked selective marker gene and growth inhibition sequence has at least one but no more than six nucleotides deleted on the side distal from the spacer sequence.

The present invention also provides a method for transforming a yeast of the genus Saccharomyces, comprising:
(1) transferring said DNA construct into yeast cells to integrate said DNA construct into a yeast chromosome by recombination between a DNA fragment capable of recombining with a yeast chromosomal DNA present in said DNA construct and the yeast chromosomal DNA,
(2) selecting yeast cells transfected with said DNA construct based on the expression of a selective marker gene contained in said DNA construct,
(3) culturing said cells in a non-selective medium to induce recombination between a pair of FRT sequences contained in said DNA construct, thereby excising the selective marker gene, and
(4) culturing said cells in a medium containing galactose to select growable yeast cells.

The present invention also provides a yeast of the genus Saccharomyces obtained by using said transformation method.

The present invention also provides a method for producing a beer using said yeast of the genus Saccharomyces.

The present invention also provides a beer obtained by said method.

BRIEF DESCRIPTION OF THE DRAWING

FIG. 3 shows a pair of FRT sequences used in the DNA construct prepared in Example 1 and reconstructed sequences generated by recombination from these sequences.

THE MOST PREFERRED EMBODIMENTS OF THE INVENTION

Figure 6:
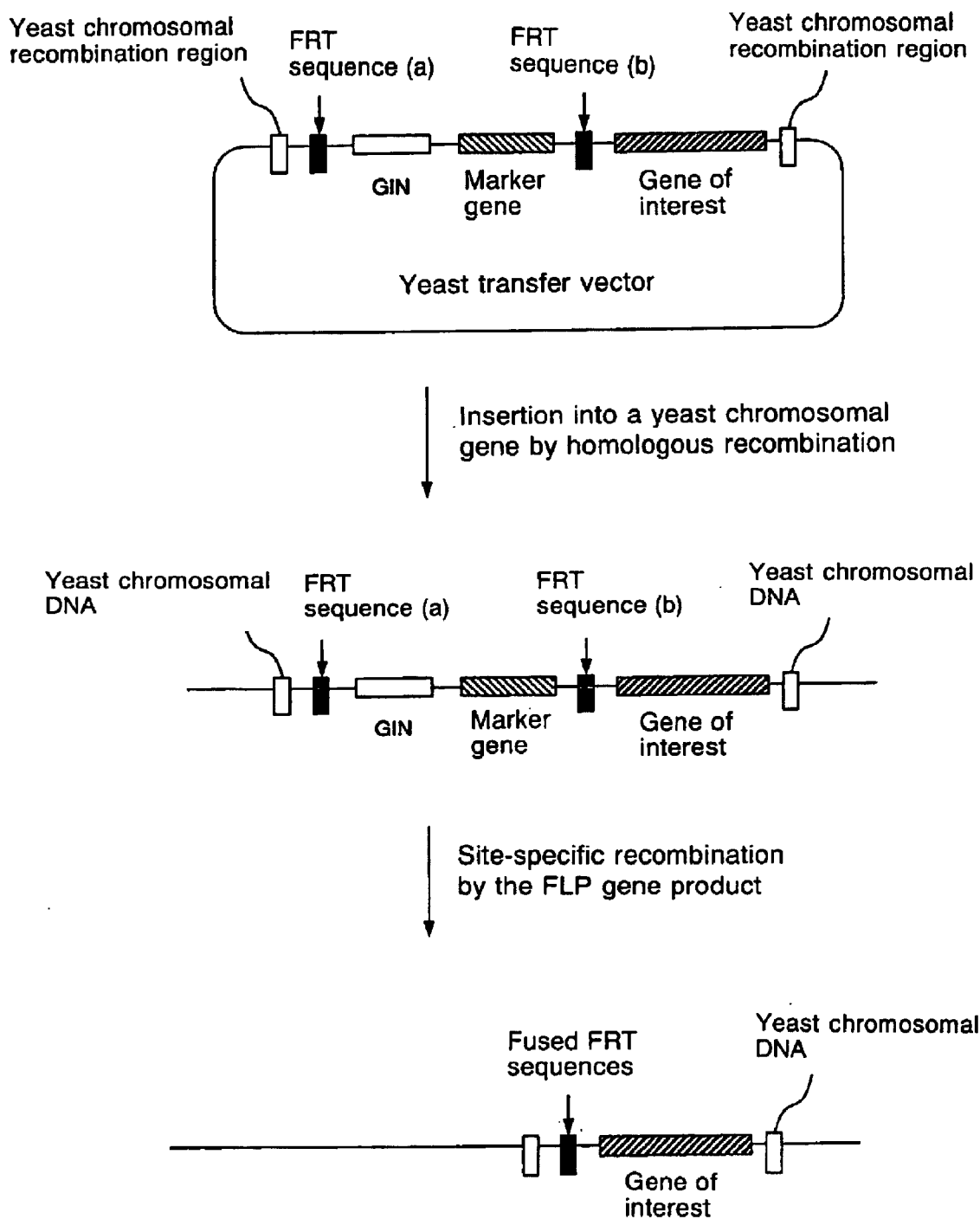
FIG. 6 is a schematic view showing the removal of a selective marker gene by site-specific recombination using a DNA construct of the present invention.

A DNA construct of the present invention and a method for transforming a yeast of the genus Saccharomyces using it are schematically shown in FIG. 6. As shown in FIG. 6, the DNA construct of the present invention comprises:
(1) a selective marker gene,
(2) a galactose-inducible growth inhibition sequence (GIN),
(3) a pair of FRT sequences in the same orientation flanking (1) and (2), and
(4) a DNA fragment capable of recombining with a yeast chromosomal,DNA located at each end of (3).

The FRT sequences in the DNA construct of the present invention contain the following sequence: 5'-<u>GAAGTTCCTATAC</u> TTTCTAGA <u>GAATAGGAACTTC</u>-3' (SEQ ID NO: 1)

| inverted repeat (1) | spacer sequence | inverted repeat (1) |
| --- | --- | --- | or a sequence substantially identical to said sequence, provided that in each member of said pair of FRT sequences, the inverted repeat distal from the flanked selective marker gene and growth inhibition sequence has at least one but no more than six nucleotides deleted on the side distal from the spacer sequence. The number of nucleotide deletions may be the same or different in the respective members of said pair of FRT sequences.

Thus, one FRT sequence (a) of a pair of FRT sequences in FIG. 6 lacks 1–6 nucleotides distal from the spacer sequence in the inverted repeat distal from the selective marker gene and growth inhibition sequence.

The other FRT sequence (FRT sequence (b) in FIG. 6) lacks 1–6 nucleotides distal from the spacer sequence in the inverted repeat distal from the selective marker gene and growth inhibition sequence.

In FRT sequences in the DNA construct of the present invention, the number of nucleotides that can be "deleted" in the above sense of the term is 1–6, preferably 2–5, more preferably 3–5, of the nucleotides (13 in total) that form the repeat adjacent to the spacer sequence. Deletion of more than 6 nucleotides is not preferred because DNA recombination very scarcely occurs.

The FRT sequence used in the present invention contains a sequence shown as SEQ ID NO: 1 wherein one inverted repeat is shortened. However, the inverted repeat opposed to the shortened inverted repeat desirably maintains 13 nucleotides and may be extended by an additional repeat. Similarly to natural FRT sequences having a structure containing the sequence shown as SEQ ID NO: 1 extended by a 13-bp repeat at one end, the inverted repeat opposed to the inverted repeat shortened as above may also be repeated in FRT sequences of the present invention.

FRT sequences used in the present invention include not only those having the sequence defined above but also those having a nucleotide sequence substantially identical to said sequence. As used herein, the 'substantially identical sequences means a sequence that can be recognized by the Flp protein to induce recombination between FRT sequences, such as a nucleotide sequence obtained by modifying the sequence defined above by substitution, deletion or addition of one or several nucleotides.

Figure 4:
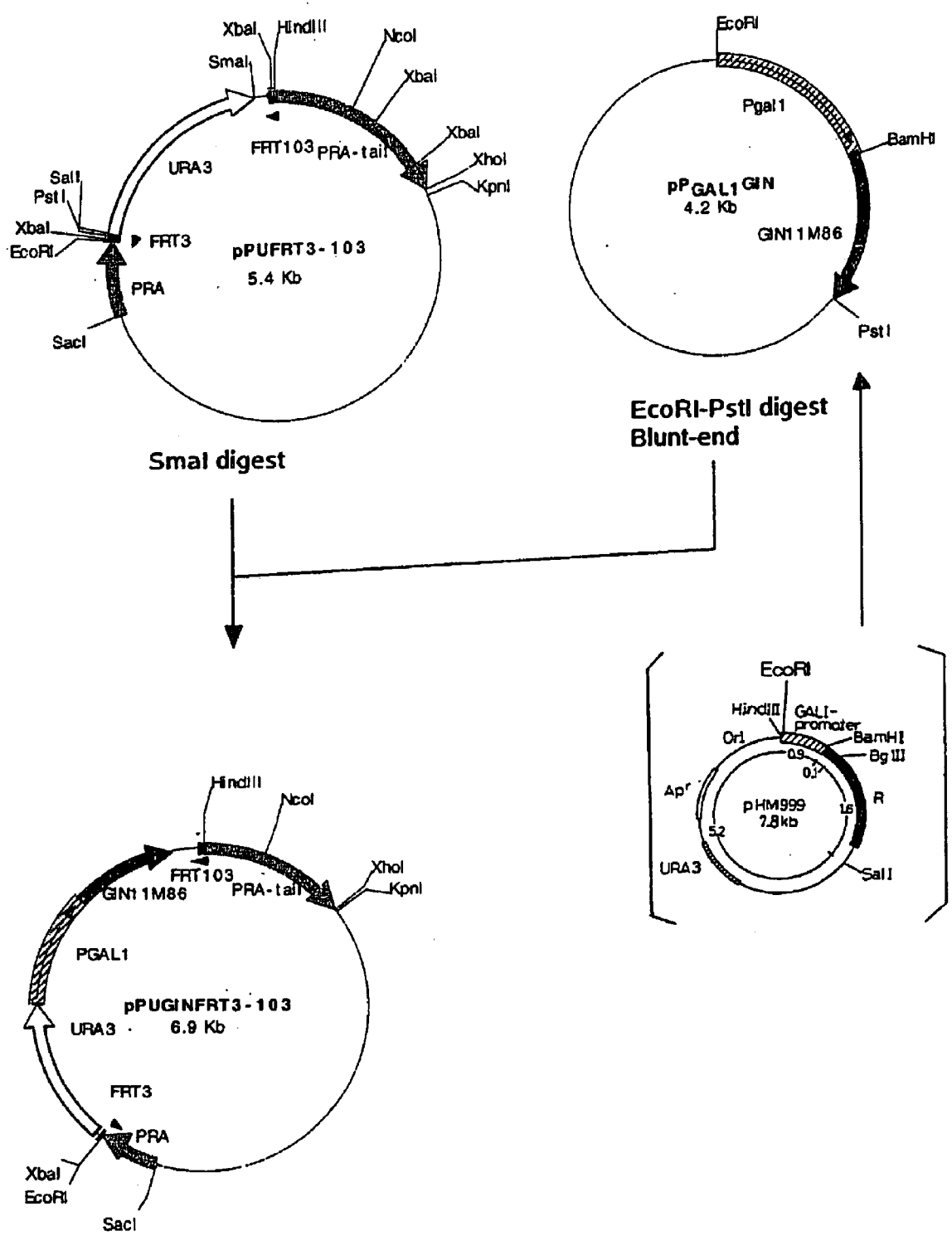
FIG. 4 is a schematic view showing the construction of plasmid pPUGINFRT3-103.

In pPUGINFRT3-103 (FIG. 4) representing the structure of an example of DNA construct of the present invention, FRT3 (SEQ ID NO: 5) in FIG. 4 of a pair of FRT sequences lacks 5 nucleotides distal from the spacer sequence in the inverted repeat distal from the selective marker gene and the growth inhibition sequence while 13 nucleotides are maintained in the inverted repeat proximal to the selective marker gene and growth inhibition sequence.

In pPUGINFRT3-103 shown in FIG. 4, the arrows shown near FRT3 and FRT103 indicate their orientation. Specifically, FRT3 in FIG. 4 is inserted with the 3' end of FRT3 in FIG. 3 being on the PRA side and the 5' end in FIG. 3 being on the URA3 side. FRT103 in FIG. 4 is inserted with the 3' end of FRT103 in FIG. 3 being on the GIN11M86 side and the 5' end in FIG. 3 being on the PRA-tail side.

The other FRT sequence (FRT103 in FIG. 4) (SEQ ID NO: 6) lacks 4 nucleotides distal from the spacer sequence in the inverted repeat distal from the selective marker gene and the growth inhibition sequence, while 13 nucleotides are maintained in the inverted repeat proximal to the selective marker gene and the growth inhibition sequence.

When a recombinase expressed by the FLP gene on the 2 μm plasmid carried by yeast acts on the DNA construct having a pair of FRT sequences as described above, DNA recombination occurs.

As a result, the selective marker gene and the growth inhibition sequence are removed and a sequence is reconstructed in which the shortened region of one FRT sequence (FRT3, for example) and the shortened region of the other FRT sequence (FRT103, for example) are fused. This reconstructed sequence has a shortened inverted repeat at each end of the spacer sequence, such as FRT3W sequence shown in FIG. 3 (SEQ ID NO: 7) reconstructed from FRT3 sequence and FRT103 sequence.

A pair of FRT sequences used in a DNA construct prepared in the examples below and sequences reconstructed by recombination from these sequences are illustrated in FIG. 3. Among them, combinations FRT2/FRT102 and FRT3/FRT103 are preferred pairs of FRT sequences for use in DNA constructs of the present invention. However, it was found that when the combination of FRT4 and FRT104 was used as a pair of FRT sequences to prepare a DNA construct, each of which lacks 7 nucleotides distal from the spacer La sequence in the inverted repeat distal from the selective marker gene and the growth inhibition sequence, the resulting DNA construct showed a low recombination efficiency.

As shown in Example 1, the FRT sequence having an inverted repeat shortened only at one side of the spacer sequence induces recombination by the action of the FLP gene product on the 2 μm plasmid carried by yeast, but the FLP gene product-induced recombination is less likely to occur when the inverted repeats on both sides are shortened (such as FRT3W sequence).

In DNA constructs of the present invention, the selective marker gene can be excised and yeast cells capable of growing in a medium containing galactose can be selected by combining said FRT sequences and galactose-inducible growth inhibition sequence.

The galactose-inducible growth inhibition sequence as used herein means a sequence encoding an RNA or a protein which inhibits growth of cells cultured in a medium containing galactose. For example, GIN11 used in the examples of the present invention was isolated as one of DNA fragments that inhibit cell growth when they are highly expressed in cells of the yeast Saccharomyces (R. Akada et al., Mol. Gen. Genet., 254, 267–274, 1997). Other genes or DNA sequences than GIN11 that suppress or inhibit cell growth can also be used, such as GIN4, URA2, BNI1, PSP1, BOI1, RBP1, SAC7, TPK3, PRK1 (R. Akada et al., Mol. Gen. Genet., 254, 267–274, 1997), ACT1, ARF2, ATE1, AUA1, ERG6, HSF1, MCM1, NHP6A, NTH1, RHO1, SEC17, SIR1, SRP40 (C. Espinet et al., Yeast, 11, 25–32, 1995).

In order to integrate a growth inhibition sequence into a DNA construct of the present invention, it can be linked to an appropriate promoter such as the GAL1 promoter and inserted.

A selective marker gene and a growth inhibition sequence are flanked by a pair of FRT sequences and it does not matter whether the selective marker gene or the growth inhibition sequence is located upstream.

The selective marker gene used may be any selective marker gene suitable for use in yeast, such as the geneticin resistance gene selectable in geneticin-containing medium or other drug resistance genes such as cerulenin resistance gene, cycloheximide resistance gene, or auxotrophy-based selective marker genes such as URA3, LEU2, TRP1 or HIS4. As shown in the examples described later, selective marker genes, whether they were based on auxotrophy or drug resistance, could be efficiently excised in the present invention by inducing recombination between the FRT sequences in pair that are contained in DNA constructs of the present invention.

The DNA fragment capable of recombining with a yeast chromosomal DNA is a DNA fragment having homology with a part of a gene on a yeast chromosome, and the gene on a yeast chromosome is such a gene that the growth of yeast is not inhibited even if it is broken, such as protease A gene, ribosomal DNA gene, CYC7 gene.

In the present invention, a gene of interest is preferably inserted between a DNA fragment capable of recombining with a yeast chromosomal DNA and an FRT sequence adjacent to said DNA fragment.

DNA constructs of the present invention can be prepared by methods known to those skilled in the art, specifically the method described in Sambrook et al., Molecular Cloning (Cold Spring Harbor Laboratory Press, 1989), for example.

The present invention also provides a method for transforming a yeast of the genus Saccharomyces using said DNA construct. This method comprises:

(1) transferring said DNA construct into yeast cells to integrate said DNA construct into a yeast chromosome by recombination between a DNA fragment capable of recombining with a yeast chromosomal DNA present in said DNA construct and the yeast chromosomal DNA, (2) selecting yeast cells transfected with said DNA construct based on the expression of a selective marker gene contained in said DNA construct, (3) culturing said cells in a non-selective medium to induce recombination between a pair of FRT sequences contained in said DNA construct, thereby excising the selective marker gene, and (4) culturing said cells in a medium containing galactose to select growable yeast cells.

This transformation procedure can be repeated a plurality of times to transfer a plurality of genes of interest into a yeast chromosome using the same selective marker gene as described below. In said method, the DNA construct can be transferred into yeast cells as a DNA fragment consisting of or containing said DNA construct or as a plasmid bearing said DNA construct. This transfer can be accomplished by any known methods such as the lithium acetate method, lithium chloride method, protoplast method, etc.

Suitable yeasts of the genus Saccharomyces include *Saccharomyces cerevisiae, Saccharomyces carlsbergensis, Saccharomyces bayanus, Saccharomyces pastrianus, Saccharomyces diastatlcus*, etc.

Then, the selective marker gene contained in the DNA construct is expressed to select yeast cells transfected with said DNA construct from transformants. Then, these cells are cultured in a non-selective medium such as a complete nutrient medium, YPD medium (2% glucose, 2% peptone, 2% yeast extract) to induce recombination between a pair of FRT sequences in some cells by the action of the Flp recombinase, which is an expression product of the FLP gene in yeast cells. Cells that have not undergone recombination between FRT sequences are inhibited from growth in a medium containing galactose, which induces expression of a growth inhibition sequence. Therefore, cells capable of growing in a medium containing galactose have undergone recombination between FRT sequences integrated on a chromosome so that the selective marker gene and the growth inhibition sequence inserted between said FRT sequences have been removed. Thus, preferred transformant yeast cells deprived of the selective marker gene can be obtained.

Figure 7:
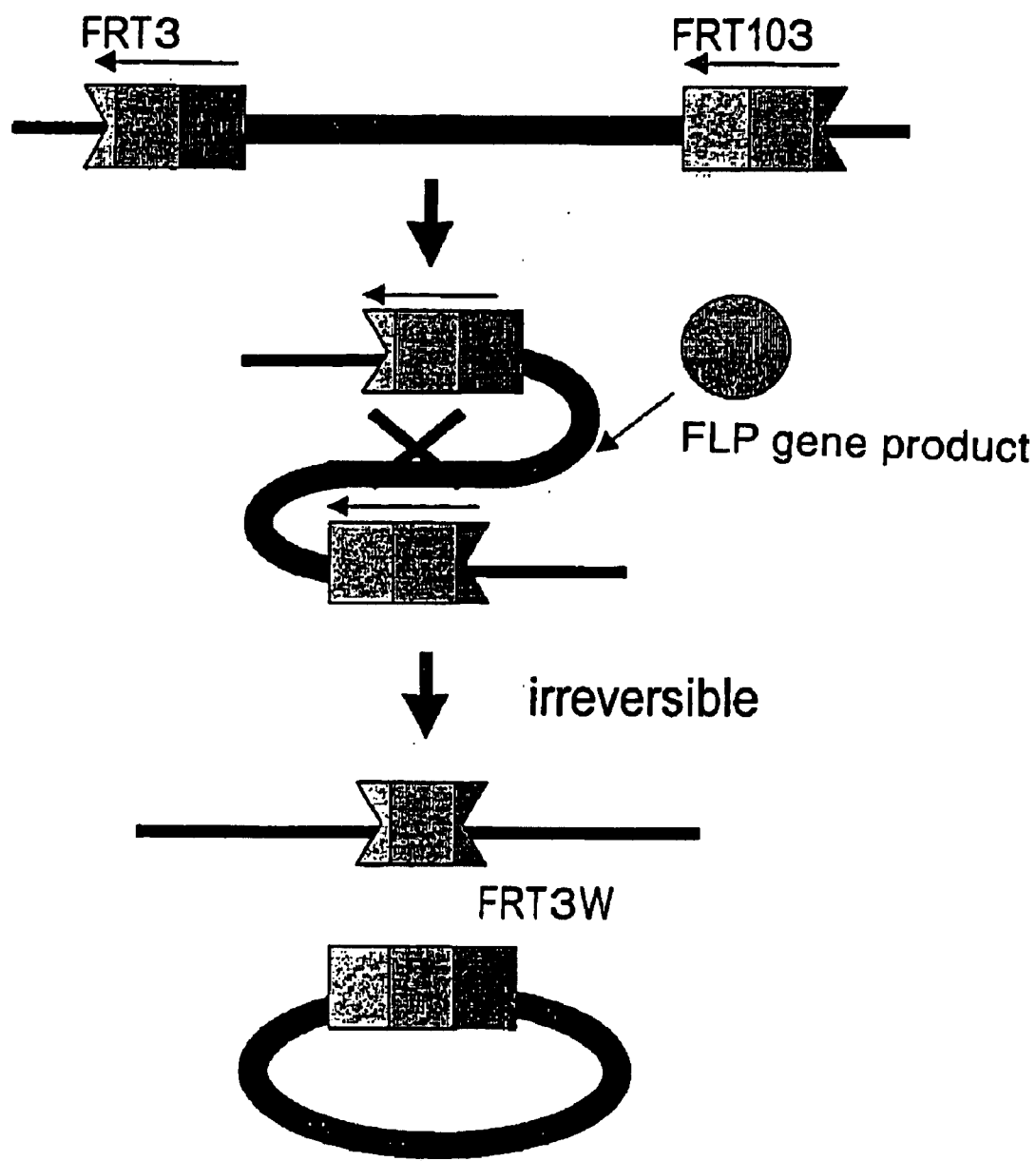
FIG. 7 is a schematic view showing that the sequence remaining after recombination is hardly recognized by the FLP gene product when a pair of FRT sequences each lacking several outer nucleotides viewed from the selective marker gene and growth inhibition sequence is used.

According to the method of the present invention, transformation is performed using a DNA construct containing an expressible selective marker gene and a galactose-inducible growth inhibition sequence inserted between FRT sequences in the same orientation, e.g., a DNA fragment, plasmid or other vectors, and a pair of FRT sequences as defined above are used to make the sequence remaining after recombination to be hardly recognized by the FLP gene product, whereby the possibility of inducing undesired recombination is reduced and the selective marker gene can be specifically removed from transformants to give desired transformants (see FIG. 7). In the present invention, any foreign recombinase gene need not be introduced because the FLP gene is present on the 2 µm plasmid of yeast itself, as described above.

The use of the method of the present invention allows selective marker genes to be removed without needing subcultures or additional transformation or mating. Safety evaluation on selective marker genes can be omitted so that development period can be shortened and development costs can also be reduced. A transformant lacking a selective marker gene can be transformed again with the same selective marker gene so that a plurality of genes can be repeatedly introduced. When a gene of interest encoding a useful protein is to be introduced into the chromosome of yeast, the method of the present invention can be used as follows.

In DNA constructs of the present invention, a DNA fragment capable of recombining with a yeast chromosomal DNA (also sometimes referred to as yeast chromosomal recombination region) is directly or indirectly linked to each end of a DNA fragment containing a pair of FRT sequences arranged as above to flank the pair of FRT sequences. When the FRT sequences and a right or left border are indirectly linked, a gene of interest to be integrated into the yeast chromosome is inserted between them (see FIG. 6). Once this DNA construct is transferred into yeast, recombination occurs between the yeast chromosomal recombination region of this DNA construct and the chromosomal gene corresponding to yeast, whereby the DNA construct is integrated as a whole into the yeast chromosomal DNA.

Then, this yeast is cultured to produce the FLP gene product on the 2 µm plasmid of yeast itself, which acts on the FRT sequence to induce site-specific recombination between a pair of FRT sequences as described above, whereby the region flanked by said pair of FRT sequences (the region containing a selective marker gene and a growth inhibition sequence) is removed and the gene of interest between the FRT sequences (cut at both ends) fused by recombination and yeast chromosomal recombination region remains as integrated in the yeast chromosomal gene. Said FRT sequence cut at both ends undergoes no more recombination so that the gene of interest inserted is stably kept in the yeast chromosome.

Thus, according to the present invention, a gene of interest is inserted into a yeast chromosome and then a is selective marker gene (as well as a growth inhibition sequence) is removed and FRT sequences get out of function. Therefore, after a gene of interest is once introduced, the gene of interest can be further introduced using a gene transfer vector containing the same selective marker gene (DNA construct of the present invention).

The present invention also provides a method for producing liquors, especially beer using a yeast stably transfected with a gene of interest by the method described above. Genes of interest may be various genes for improving the quality of beer or brewing processes.

For example, off flavor is generated by the metabolism of yeast during beer brewing. The amount of such off flavor generated can be decreased or deleted by controlling the expression of a specific gene for brewing yeast. For example, off flavor of beer is derived from hydrogen sulfide and VDK (diacetyl and 2,3-pentadione). Hydrogen sulfide is an intermediate metabolite of the sulfur assimilation path and it is difficult to control its generation during beer brewing using typical brewer's yeasts. However, it was reported that the generation of hydrogen sulfide during beer brewing can be controlled by overexpressing the MET25 gene of brewer's yeasts via gene recombination techniques (JPA 303475/95). Another example of off flavor VDK is an intermediate metabolite of the branched amino acid synthesis path, and it was also reported that VDK generation can be controlled by overexpressing the ILV5 gene of yeast via gene recombination techniques (S. M. Mithieux and A. S. Weiss, Yeast 11:311–316, 1965).

As described above, some yeast breeds with controlled off flavor using gene recombination techniques are known from documents, but no breed has been applied to commercial production in actual plants. A reason why valuable bred yeasts are not applied commercial production lies in the presence of DNA fragments derived from selective marker genes or microorganisms other than yeasts in the DNA of recombinant yeast.

In the present invention, undesirable sequences can be removed after transformation by inserting FRT sequences at both ends of selective marker genes or other undesirable DNA sequences. As a result, selective marker genes can be reused, and therefore, a plurality of genes can be introduced into brewer's yeasts with few kinds of selective marker genes, whereby the variety of brewer's yeast breeds is considerably broadened. For example, the ILV5 gene and MET25 gene mentioned above as different breeding examples can be individually introduced into the same yeast cells to attain yeast breeds in which generation of both hydrogen sulfide and VDK is controlled. In addition, transformed brewer's yeasts obtained by the present invention, which contain no DNA sequences other than those of brewer's yeasts, may readily find social acceptance so that they can be applied to commercial production.

Obviously, the present invention can be applied to not only yeast breeds in which off flavor is removed but also other breeds in which brewing efficiency is improved. For example, efficient brewing can be achieved by enhancing the transporter of sugars (Y. Kodama, J. Am. Soc. Brew. Chem., 53:24–29, 1995) or amino acids by gene recombination to improve fermentation speed or conferring resistance to stresses such as osmosis or alcohols by genetic engineering to produce highly concentrated alcohols. The present invention can also be applied to these breeds to produce similar effects to those described for removal of off flavor.

In the present invention, it was confirmed that selective marker genes can be efficiently removed in not only haploid yeasts but also brewer's diploid yeasts, which promises the application of the present invention to actual beer brewing.

EXAMPLES

The following examples further illustrate the present invention. However, these examples are given only for illustrative purpose but not intended to limit the scope of the invention. Experimental procedures were based Molecular Cloning of Sambrook et al. (Cold Spring Harbor Laboratory Press, 1989) unless otherwise specified.

Example 1

Study of Excision Efficiency of a Selective Marker Gene Using FRT Sequences (1) Construction of a Plasmid Containing Wild-type FRT Sequences The following 4 oligonucleotides were synthesized to insert FRT sequences into the plasmid (with wild-type FRT sequences underlined).

FRT1-a
5'-TCGACGAAGTTCCTATACTTTCTAGAGAATAGG-AACTTCG-3' (SEQ ID NO: 11)
FRT1-b
5'-AATTCGAAGTTCCTATTCTCTAGAAGTATAGGA-ACTTCG-3' (SEQ ID NO: 12)
FRT101-a
5'-AGCTTGAAGTTCCTATACTTTCTAGAGAATAGG-AACTTCGCATG-3' (SEQ ID NO: 13)
FRT101-b
5'-CGAAGTCCTATTCTCTAGAAAGTATAGGAACTT-CA-3' (SEQ ID NO: 14).

Figure 1:
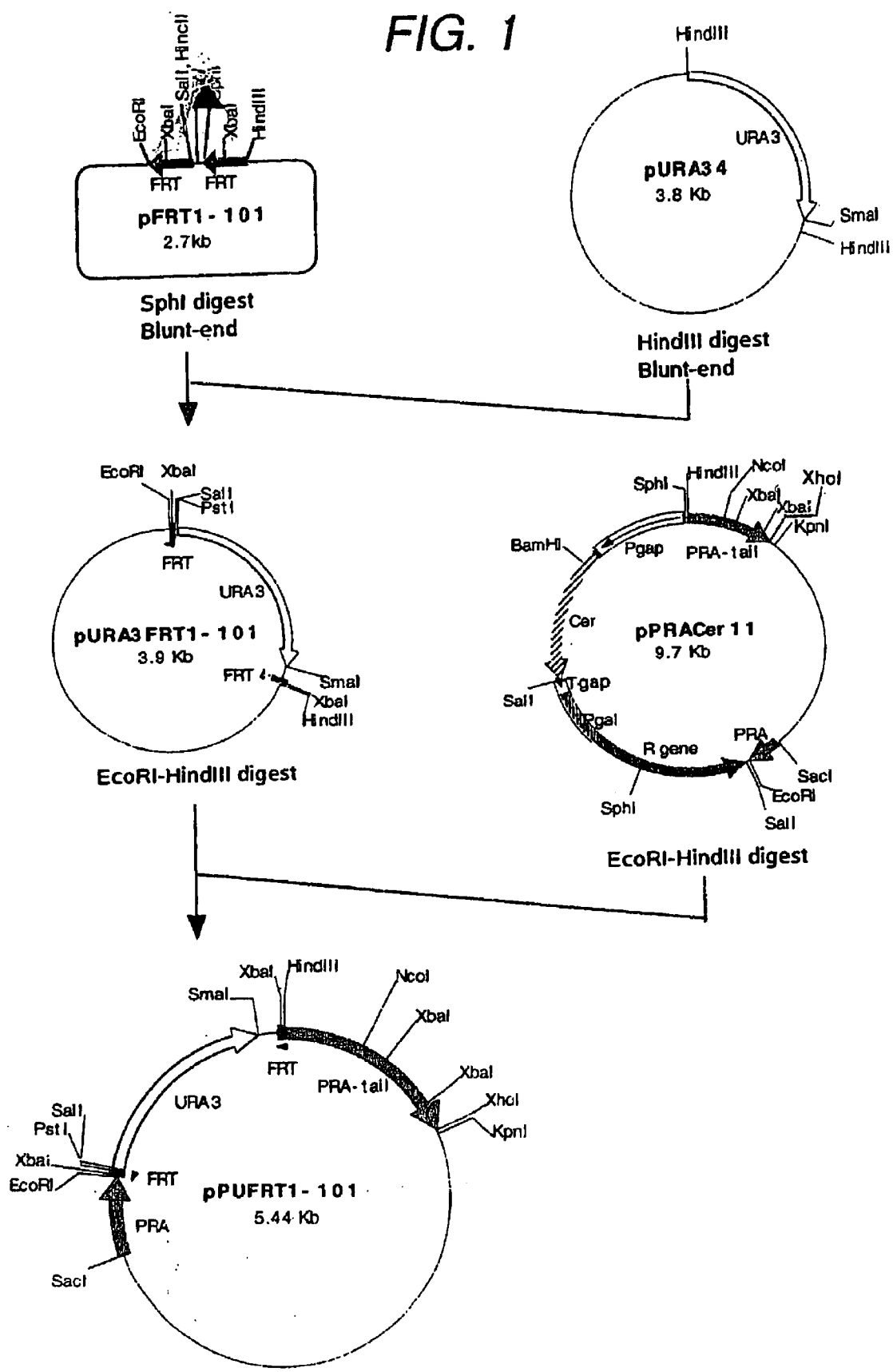
FIG. 1 is a schematic view showing the construction of plasmid pPUFRT1-101 containing wild-type FRT sequences.

After phosphorylation of the ends of these synthetic DNAs, FRT1-a was annealed to FRT1-b and FRT101-a was annealed to FRT101-b, and the former annealed product was inserted at a restriction endonuclease EcoRI-SalI site and then the latter annealed product was inserted at a restriction endonuclease SphI-HindIII site of pUC18 (Toyobo) to construct a plasmid pFRTl-101 (FIG. 1).

The selective marker gene used was the URA3 gene. Strains bearing the URA3 gene can be selected by the character of Ura+ while ura3 strains deprived of the URA3 gene can be selected by 5-fluoroorotic acid resistance, so that ura3 strains can be used as hosts to readily determine both strains bearing and deprived of the selective marker gene URA3.

Separately, pUC18 was digested with restriction endonucleases EcoRI and SphI and blunt-ended with Blunting Kit (Takara Shuzo), and then self-ligated to construct pUC18HSp. A 1.2-kb restriction endonuclease HindIII fragment containing the URA3 gene of YEp24 (Botstein, D., et al., Gene, 8, 17, 1979) was inserted at this restriction endonuclease HindIII site to construct pURA34 (FIG. 1).

pFRT1-101 was digested with restriction endonuclease SphI and then blunt-ended with Blunting Kit (Takara Shuzo), and then ligated to a fragment of about 1.2 kb obtained by digesting pURA34 with restriction endonuclease HindIII and then blunt-ending it with Blunting Kit (Takara Shuzo) to construct a plasmid pURA3FRT1-101 (FIG. 1).

A DNA fragment of about 1.2 kb obtained by treating pURA3FRT1-101 with restriction endonucleases EcoRI and HindIII and a fragment of about 4.2 kb obtained by treating pPRACer11 (FIG. 1) with EcoRI and HindIII were ligated to construct a plasmid pPUFRT1-101 (FIG. 1). pPRACer11 was constructed by inserting an HindIII-SalI fragment excised from pHM153 (J. Bacteriol., 172, 610–618, 1990), the Cer resistance gene (obtained as a DraI-KpnI fragment of about 1.7 kb of PDR4: Gene, 101, 149–152, 1991) flanked by a gap terminator and a gap promoter (Appl. Microbiol. Biotechnol., 32, 129–133, 1989), and protease A genes (PRA) consisting of an SacI-EcoRI fragment and an HindIII-XhoI fragment of plasmid CBZ1 (Mol. Cell. Biol., 6, 2500–2510, 1986) into pBluescript SK- (Toyobo).

(2) Construction of Plasmids Containing FRT Sequences Lacking Several Outer Nucleotides Viewed from the Selective Marker Gene as Compared with Wild-type FRT Sequences Then, plasmids in which the wild-type FRTs of pPUFRT1-101 are replaced by FRT sequences of various lengths prepared with synthetic DNAs are prepared. The sequences of the synthetic DNAs used are shown below.

FRT2-a: 5'-CTAGAGAATAGGAACG-3' (SEQ ID NO: 15)
FRT2-b: 5'-AATTCGTTCCTATTCT-3' (SEQ ID NO: 16)
FRT102-a: 5'-AGCTTGTTCCTATACTTT-3' (SEQ ID NO: 17)
FRT102-b: 5'-CTAGAAAGTATAGGAACA-3' (SEQ ID NO: 18)
FRT3-a: 5'-CTAGAGAATAGGAG-3' (SEQ ID NO: 19)
FRT3-b: 5'-AATTCTCCTATTCT-3' (SEQ ID NO: 20)
FRT103-a: 5'-AGCTTTCCTATACTTT-3' (SEQ ID NO: 21)
FRT103-b: 5'-CTAGAAAGTATAGGAA-3' (SEQ ID NO: 22)
FRT4-a: 5'-CTAGAGAATAGG-3' (SEQ ID NO: 23)
FRT4-b: 5'-AATTCCTATTCT-3' (SEQ ID NO: 24)
FRT104-a: 5'-AGCTTCTATACTTT-3' (SEQ ID NO: 25)
FRT104-b: 5'-CTAGAAAGTATAGA-3' (SEQ ID NO: 26).

Figure 2:
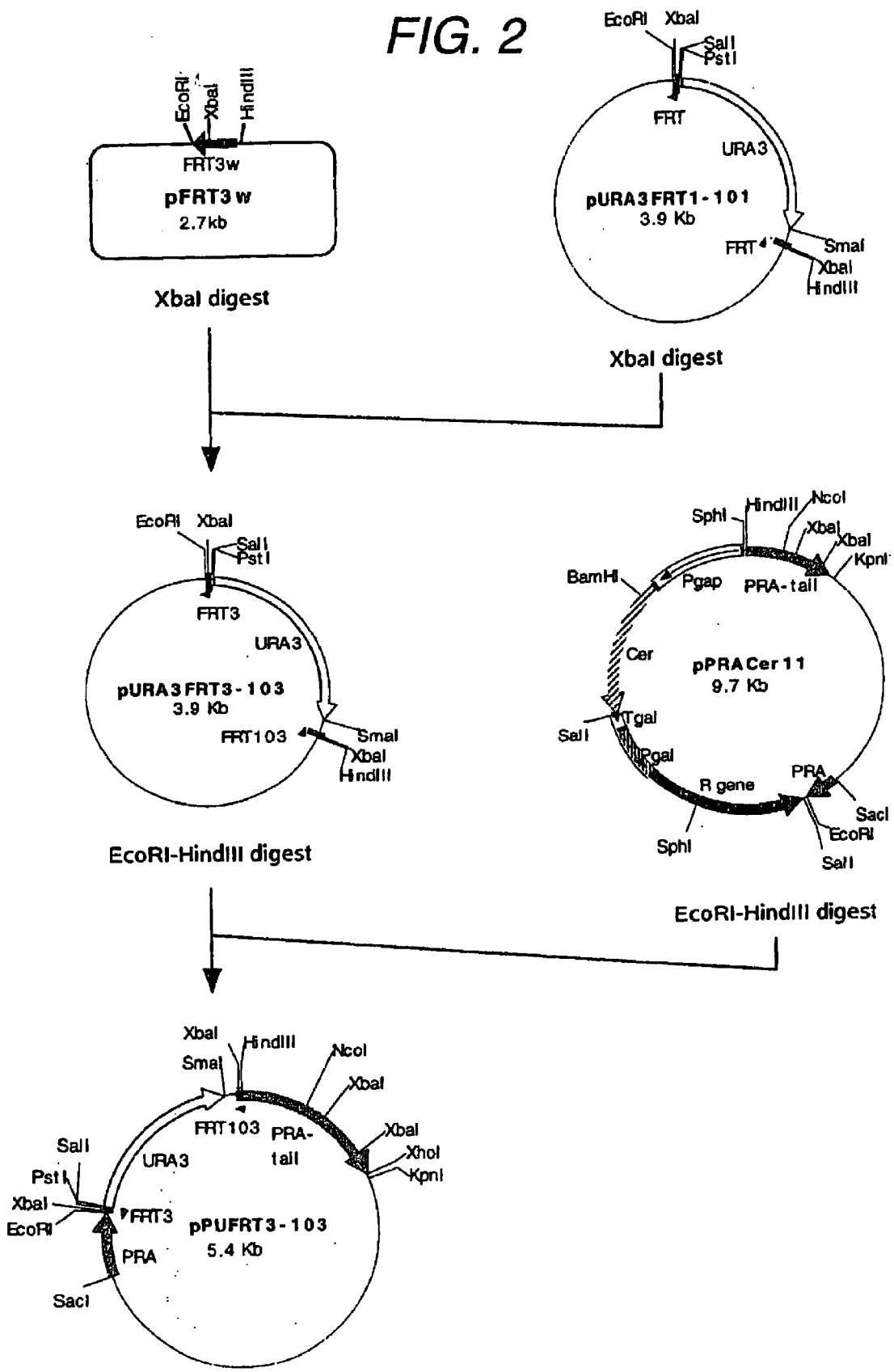
FIG. 2 is a schematic view showing the construction of plasmid pPUFRT3-103.

Synthetic DNAs of the above sequences were 5′ end-phosphorylated, and then annealed into combinations of FRT2-a/FRT2-b/FRT102-a/FRT102-b, FRT3-a/FRT3-b/FRT103-a/FRT103-b, and FRT4-a/FRT4-b/FRT104-a/FRT104-b, which were each inserted at an EcoRI-HindIII site of pUC18 to construct plasmids pFRT2w, pFRT3w (FIG. 2) and pFRT4w. In the process above, W sequences deleted at both ends were prepared by annealing 4 synthetic DNAs and inserted Into a plasmid, among which a W sequence obtained from the combination of FRT3-a/FRT3-b/FRT103-a/FRT103-b is shown below, as an example.

TABLE 1

| FRT sequence | Recombination frequency |
|---|---|
| FRT1-FRT101 (wild-type) | 1/3–1/2 |
| FRT2-FRT102 | $1/10^3$–$1/10^4$ |
| FRT3-FRT103 | $1/10^5$–$1/10^6$ |
| FRT4-FRT104 | $<1/10^7$ |

It was shown from Table 1 that in vivo recombination efficiency is ½ or less even with a combination of wild-type

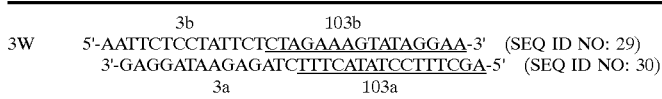

A fragment of about 1.2 kb obtained by treating plasmid pURA3FRT1-101 with XbaI at an XbaI site of these plasmids (pFRT2w, pFRT3w, pFRT4w) to construct plasmids pURA3FRT2-102, pURA3FRT3-103 (FIG. 2) and pURA3FRT4-104. These plasmids contain the selective marker gene URA3 between a pair of FRT sequences in the same orientation each lacking several outer nucleotides viewed from the selective marker gene as compared with the counterpart wild-type FRT sequence.

Thus obtained FRT sequences and FRT sequences generated after excision with combinations thereof are listed in FIG. 3.

Fragments of about 1.2 kb obtained by treating these plasmids with EcoRI and HindIII were ligated to a fragment of about 4.2 kb obtained by treating pPRACer11 with EcoRI and HindIII to construct plasmids pPUFRT2-102, pPUFRT3-103 (FIG. 2) and pPUFRT4-104.

(3) Examination of In Vitro Recombination Frequency

A haploid yeast strain R27-7C-1C (MATα trp1 leu2 his3 ura3) was used. Transformation of yeast can be accomplished by the method using lithium chloride (Kodama, Y., et al., J. Am. Soc. Brew. Chem., 53, 24–29, 1995).

About 10 μg each of pPUFRT1-101, pPUFRT2-102, pPUFRT3-103 and pPUFRT4-104 was treated with KpnI and SacI and ethanol-precipitated, and then dissolved in 10 μl of TE buffer, and the total amount of the solution was used for recombination of the yeast to select strains transformed to Ura⁺. That is, yeast cells transformed as above are plated onto a Ura⁻ selective medium (Yeast Nitrogen Base [(NH₄)₂SO₄] (DIFCO), 2% glucose, 0.01% leucine, 0.01% tryptophan, 2% agar), and incubated at 30° C. for 72 hours.

Thus obtained transformed strains were cultured on YPD liquid medium at 30° C. overnight to induce recombination between two FRT sequences integrated on a chromosome by a recombinase expressed by the FLP gene on the 2 μm plasmid carried by strain R27-7C-1C.

The culture medium was appropriately diluted in sterilized water and 100 μl of the dilution was plated on YPD agar medium and an agar medium containing 5-fluoroorotic acid (Yeast Nitrogen Base [(NH₄)₂SO₄] (DIFCO). 2% glucose, 0.005% uracil, 0.01% leucine, 0.01% tryptophan, 0.1% 5-fluoroorotic acid, 2% agar), and incubated at 30° C. for 48 hours, after which the number of appearing colonies was counted. Cells capable of growing on the medium containing 5-fluoroorotic acid are cells which have undergone recombination. The results are shown in Table 1.

FRT sequences and that the frequency sharply decreases as deletion increases.

Example 2

Study of Excision Efficiency of a Selective Marker Gene Using a Combination of FRT Sequences and GIN11

(1) Construction of Plasmid pPUGINFERT3-103

Two oligonucleotides were synthesized to prepare a plasmid containing GIN11.

GIN-1:
5′-TGGATCCGGAATTTCGACGGATCAATAAC-3′ (SEQ ID NO: 27)

GIN-2:
5′-TTCTGCAGACTAGATGCACTCATATCATTATG-CAC-3′ (SEQ ID NO: 28).

A fragment of about 0.7 kb obtained by PCR on plasmid pAUR135 (Takara Shuzo) as a template using these oligonucleotides as primers was treated with BamHI and PstI, and inserted at an EcoRI-PstI site of pUC19 together with a fragment of about 0.8 kb containing the GAL1 promoter obtained by treating pRM999 (JPA 66587/98) with EcoRI and BamHI to construct a plasmid pPGAL1GIN (FIG. 4) containing GIN11M86 (Takara Shuzo) linked to the GAL1 promoter.

A fragment of about 1.5 kb obtained by treating said plasmid with EcoRI and PstI was blunt-ended with Blunting Kit (Takara Shuzo) and then inserted at an SmaI site of pPUFRT3-103 to give a plasmid pPUGINFRT3-103 (FIG. 4).

(2) Removal of the Selective Marker Gene Using a Laboratory Strain

A haploid yeast strain R27-7C-1C (MATα trp1 leu2 his3 ura3) was used. A DNA fragment of about 4.1 kb (about 10 μg) obtained by treating plasmid pPUGINFRT3-103 with KpnI and SacI was used for recombination of the yeast and transformants were selected by the caracter of Ura⁺.

When the resulting transformants were cultured in a non-selective medium, some cells underwent recombination between FRT sequences by the action of the Flp recombinase present in the cells. However, cells that have not undergone recombination between FRT sequences are inhibited from growing in a medium containing galactose, which induces expression of GIN11M86. Therefore, cells capable of growing in a medium containing galactose have undergone recombination between FRT sequences integrated on a chromosome so that the selective marker gene and GIN11M86 linked to the GAL1 promoter inserted between said sequences have been removed.

The resulting transformants were cultured in 10 ml of YPGal liquid medium (2% peptone, 1% yeast extract, 2% galactose) at 30° C. for 24 hours to induce recombination between FRT sequences and expression of GIN11M86. The culture medium was appropriately diluted and plated on YPGal agar medium and incubated at 30° C. for 48 hours. One hundred strains of the resulting colonies were cultured on a 5-fluoroorotic acid agar medium and a Ura⁻ selective medium at 30° C. for 48 hours. As a result, all the strains failed to grow only on the Ura⁻ selective medium. This means that all the strains capable of growing on YPGal agar medium have been deprived of the URA3 gene.

Example 3

Removal of a Drug Resistance Selective Marker Gene (1) Construction of Plasmid pPPGINFRT3

Figure 5A:
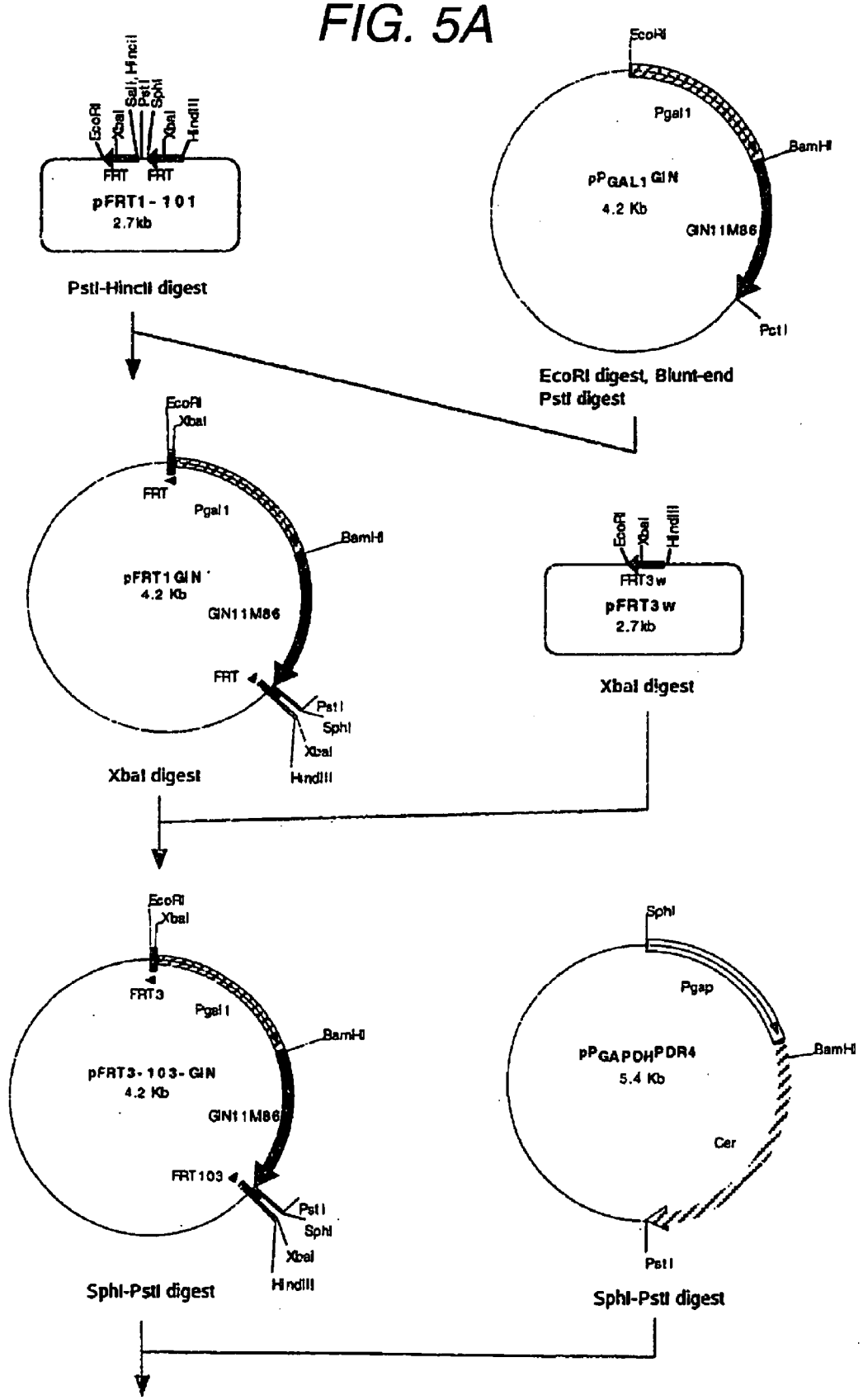
FIGS. 5A and 5B are schematic views showing the construction of plasmid pPPGINFRT3.

A selective marker gene PDR4 (cerulenin and cycloheximide resistance gene) and GIN11M86 linked to the galactose-inducible GAL1 promoter were flanked by site-specific recombination sequences (FRT3, FRT103). A fragment of about 1.5 kb obtained by treating plasmid pPGAL1GIN with restriction endonuclease EcoRI and blunt-ending it with Blunting Kit (Takara Shuzo) and then treating it with restriction endonuclease PstI was inserted at an HindIII-PstI site of plasmid pFRT1-101 to construct a plasmid pFRT1GIN (FIG. 5A). A fragment of about 1.5 kb obtained by treating pFRT1GIN with restriction endonuclease XbaI was inserted at an XbaI site of pFRT3w to give a plasmid pFRT3-103-GIN (FIG. 5A).

Figure 5B:
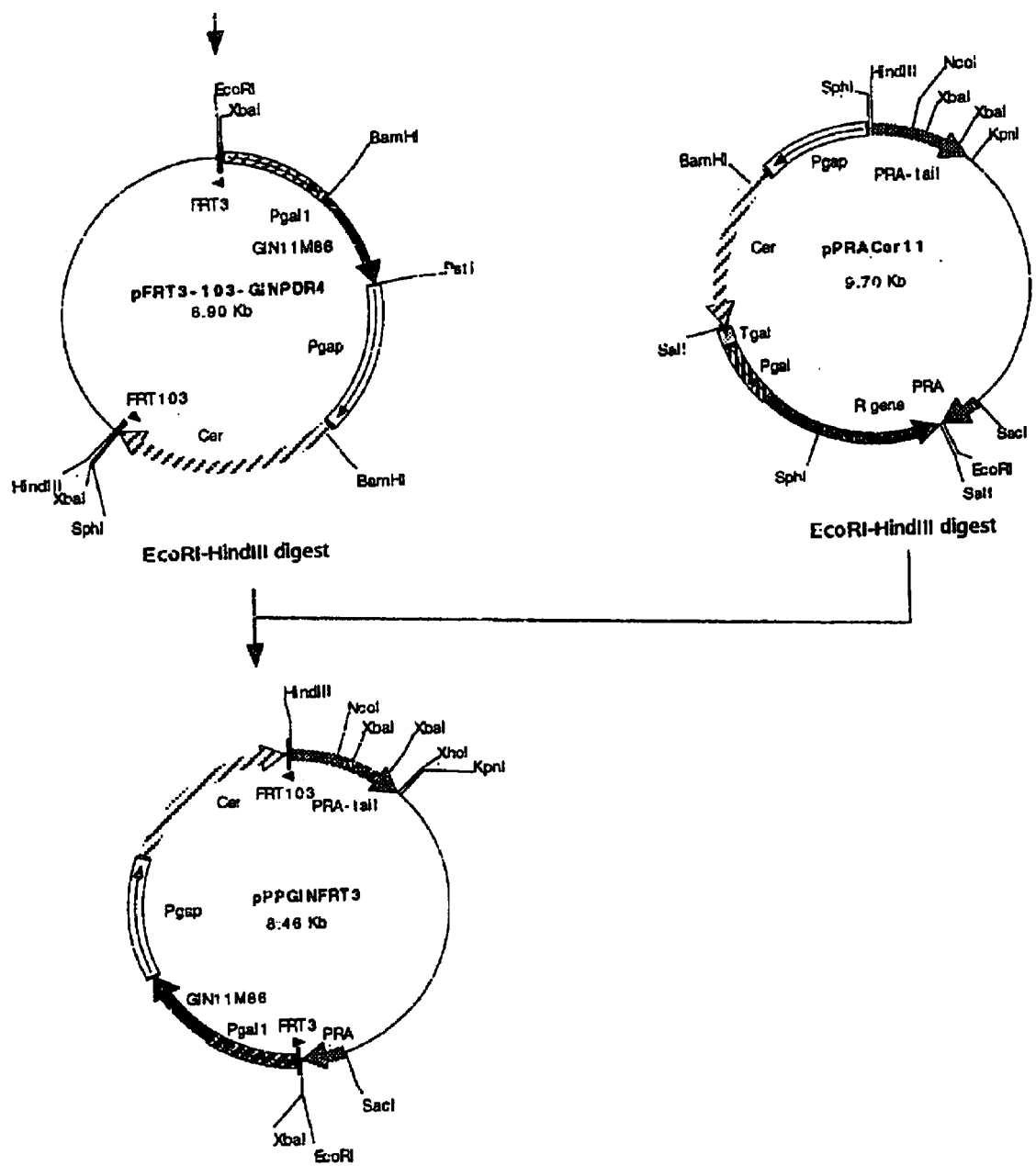

A fragment of about 2.7 kb obtained by treating pPRACer11 with SphI and SalI was inserted at an SphI-SalI site of pUC18 and then treated with SalI and blunt-ended with Blunting Kit, and a pPstI linker (Toyobo) was inserted to construct a plasmid pPGAPDHPDR4 (FIG. 5A). A fragment of about 2.7 kb obtained by treating pPGAPDHPDR4 with SphI and PstI was inserted at an SphI-PstI site of pFRT3-103-GIN to construct a plasmid pFRT3-103-GINPDR4 (FIG. 5B). A fragment of about 4.2 kb obtained by treating this plasmid with EcoRI and HindIII and a fragment of about 4.2 kb obtained by treating pPRACer11 with EcoRI and HindIII were ligated to construct a plasmid pPPGINFRT3 (FIG. 5B).

This plasmid contains GIN11 linked to a galactose-inducible promoter and the PDR4 gene linked to a constitutive promoter of yeast, glyceraldehyde 3-phosphate dehydrogenase promoter inserted between FRT3 and FRT103.

(2) Removal of the Selective Marker Gene Using a Laboratory Strain

About 10 μg of plasmid pPPGINFRT3 was treated with restriction endonucleases KpnI and SacI and ethanol-precipitated, and then dissolved in 10 μl of TE buffer, and the total amount of the solution was used for transformation. A haploid yeast strain R27-7C-1C was used as a host and transformed by the method using lithium chloride. Then, transformants were plated on a YPD plate containing 1 μg/ml cycloheximide and cultured at 30° C. for 2 days to select cycloheximide-resistant strains.

To excise the selective marker gene, a loop of transformants was inoculated on 10 ml of YPGal liquid medium and shaken-cultured at 30° C. for 24 hours. The culture medium was appropriately diluted and then plated on a YPGal plate and incubated at 30° C. for 2 days. A hundred of strains of the resulting colonies were randomly collected and replicated on a YPD plate containing cycloheximide to examine cycloheximide resistance.

As a result, 100 of 100 strains were sensitive to cycloheximide, suggesting that the selective marker gene was excised by site-specific recombination in these strains.

(3) Removal of the Selective Marker Gene Using Brewer's Yeasts (3-1) First Transformation and Removal of the Selective Marker Gene Transformants were produced by the same procedure as used with laboratory strains. The host used was a diploid wild-type yeast strain AY-1 (MATa/α wild type), though any polyploid yeast strains may be used.

A loop of colonies of the resulting transformants was inoculated on 10 ml of YPGal liquid medium and shaken-cultured at 30° C. for 24 hours. The culture medium was appropriately diluted and then plated on a YPGal plate and incubated at 30° C. for 2 days. A hundred of strains of the resulting colonies were randomly collected and replicated on a YPD agar medium containing 1 μg/ml cycloheximide to examine cycloheximide resistance.

As a result, 100 of 100 strains could not grow on the agar medium containing cycloheximide, suggesting that the selective marker gene was excised by site-specific recombination in these strains.

(3-2) Second Transformation and Removal of the Selective Marker Gene

One of the strains deprived of the selective marker gene after transformation by the procedure above was used for second transformation. Procedures of transformation and removal of the selective marker gene were the same as those of the first run.

As a result, 100 of 100 strains could not grow on the agar medium containing cycloheximide, suggesting that the selective marker gene was excised by site-specific recombination in these strains.

What is claimed is:

1. A DNA construct comprising:
   (i) a selective marker gene,
   (ii) a galactose-inducible growth inhibition sequence,
   (iii) a pair of FRT (Flp recombinase recognition target) sequences in the same orientation flanking (i) and (ii), and
   (iv) a DNA fragment capable of recombining with a yeast chromosomal DNA located at each end of (iii), wherein both of said FRT sequences have deletions of nucleotides in the following sequence:
   5'-GAAGTTCCTATAC TTTCTAGA GAATAGGMCTTC-3' (SEQ ID NO: 1)

| inverted repeat (1) | spacer sequence | inverted repeat (2) |
   |---|---|---| wherein the FRT sequence which exists at the 5' side of the selective marker gene and the GIN sequence has at least 1 but not more than 4 nucleotides deleted from the 5' end of the inverted repeat (1) thereof: and wherein the FRT sequence which exists at the 3' side of the selective marker gene and the GIN sequence has at least 1 but not more than 5 nucleotides deleted from the 3' end of the inverted repeat (2) thereof.

2. The DNA construct of claim 1,
   wherein the FRT sequence which exists at the 5' side of the selective marker gene and the GIN sequence has 3 or 4 nucleotides deleted from the 5' end of the inverted repeat (1) thereof; and wherein the FRT sequence which exists at the 3' side of the selective marker gene and the GIN sequence has 3–5 nucleotides deleted from the 3' end of the inverted repeat (2) thereof.

3. The DNA construct of claim 1,
   wherein in the case that the FRT sequence which exists at the 5' side of the selective marker gene and the GIN sequence has the following sequence (FRT102): 5'-GTTCCTATAC TTTCTAGA GAATAGGAACTTC-3' (SEQ ID NO: 3),

| inverted repeat (1) | spacer sequence | inverted repeat (2) |
   |---|---|---| the other FRT sequence which exists at the 3'side of the selective marker gene and the GIN sequence has the following sequence (FRT2): 5'-GMGTTCCTATAC TTTCTAGA GAATAGGAAC-3' (SEQ ID NO: 2); or

| inverted repeat (1) | spacer sequence | inverted repeat (2) |
   |---|---|---| wherein in the case that the FRT sequence which exists at the 5' side of the selective marker gene and the GIN sequence has the following sequence (FRT103): 5'-TTCCTATAC TTTCTAGA GAATAGGAACTTC-3' (SEQ ID NO: 6),

| inverted repeat (1) | spacer sequence | inverted repeat (2) |
   |---|---|---| the other FRT sequence which exists at the 3' side of the selective marker gene and the GIN sequence has the following sequence (FRT3): 5'-GAAGTTCCTATAC TTTCTAGA GAATAGGA-3' (SEQ ID NO: 5).

| inverted repeat (1) | spacer sequence | inverted repeat (2) |
   |---|---|---|

4. The DNA construct of any one of claims 1, 2 and 3 wherein a gene of interest is inserted between the DNA fragment capable of recombining with a yeast chromosomal DNA and a FRT sequence adjacent to said fragment.

5. A method for transforming a yeast of the genus Saccharomyces, comprising:
   (1) transferring the DNA construct of claim 1 into yeast cells to integrate said DNA construct into a yeast chromosome by recombination between the two DNA fragments and the yeast chromosomal DNA,
   (2) selecting yeast cells transfected with said DNA construct based on the expression of the selective marker gene contained in said DNA construct,
   (3) culturing said cells in a non-selective medium to induce recombination between the pair of FRT sequences contained in said DNA construct, thereby excising the selective marker gene, and
   (4) culturing said cells in a medium containing galactose to select growable yeast cells.

6. The method of claim 5 wherein said DNA construct further comprises a gene of interest between said DNA fragment and said FRT sequence adjacent to said fragment.

7. The method of claim 6 wherein the step of claim 4 is repeated to introduce a plurality of genes of interest.

8. A yeast of the genus Saccharomyces transformed by the method of any one of claims 5 to 7.

9. A method for producing a beer comprising the following steps:
   adding the yeast of the genus Saccharomyces of claim 8 to wort, and
   fermenting said wort containing the yeast.

* * * * *

SEQUENCE LISTING

<160> NUMBER OF SEQ ID NOS: 30

<210> SEQ ID NO 1
<211> LENGTH: 34
<212> TYPE: DNA
<213> ORGANISM: Artificial Sequence
<220> FEATURE:
<223> OTHER INFORMATION: FRT sequence used in present invention contains SEQ ID NO:1

```
<400> SEQUENCE: 1
gaagttccta tactttctag agaataggaa cttc                              34

<210> SEQ ID NO 2
<211> LENGTH: 31
<212> TYPE: DNA
<213> ORGANISM: Artificial Sequence
<220> FEATURE:
<223> OTHER INFORMATION: FRT2 which is one of a pair of FRT sequences
      (FRT2/FRT102) used in a DNA construct of the present invention

<400> SEQUENCE: 2
gaagttccta tactttctag agaataggaa c                                 31

<210> SEQ ID NO 3
<211> LENGTH: 31
<212> TYPE: DNA
<213> ORGANISM: Artificial Sequence
<220> FEATURE:
<223> OTHER INFORMATION: FRT102 which is one of a pair of FRT sequences
      (FRT2/FRT102) used in a DNA construct of the present invention

<400> SEQUENCE: 3
gttcctatac tttctagaga ataggaactt c                                 31

<210> SEQ ID NO 4
<211> LENGTH: 28
<212> TYPE: DNA
<213> ORGANISM: Artificial Sequence
<220> FEATURE:
<223> OTHER INFORMATION: FRT2W sequence reconstructed by recombination
      from a pair of FRT sequences (FRT2/FRT102)

<400> SEQUENCE: 4
gttcctatac tttctagaga ataggaac                                     28

<210> SEQ ID NO 5
<211> LENGTH: 29
<212> TYPE: DNA
<213> ORGANISM: Artificial Sequence
<220> FEATURE:
<223> OTHER INFORMATION: FRT3 which is one of a pair of FRT sequences
      (FRT3/FRT103) used in a DNA construct of the present invention

<400> SEQUENCE: 5
gaagttccta tactttctag agaatagga                                    29

<210> SEQ ID NO 6
<211> LENGTH: 30
<212> TYPE: DNA
<213> ORGANISM: Artificial Sequence
<220> FEATURE:
<223> OTHER INFORMATION: FRT103 is one of a pair of FRT sequences
      (FRT3/FRT103) used in a DNA construct of the present invention

<400> SEQUENCE: 6
ttcctatact ttctagagaa taggaacttc                                   30

<210> SEQ ID NO 7
<211> LENGTH: 25
<212> TYPE: DNA
<213> ORGANISM: Artificial Sequence
<220> FEATURE:
<223> OTHER INFORMATION: FRT3W sequence reconstructed by recombination
      from a pair of FRT sequences (FRT3/FRT103)

<400> SEQUENCE: 7
```

```
ttcctatact ttctagagaa tagga                                         25

<210> SEQ ID NO 8
<211> LENGTH: 27
<212> TYPE: DNA
<213> ORGANISM: Artificial Sequence
<220> FEATURE:
<223> OTHER INFORMATION: FRT4 which is one of a pair of FRT sequences
      (FRT4/FRT104) used in a DNA construct of the present invention

<400> SEQUENCE: 8
gaagttccta tactttctag agaatag                                       27

<210> SEQ ID NO 9
<211> LENGTH: 27
<212> TYPE: DNA
<213> ORGANISM: Artificial Sequence
<220> FEATURE:
<223> OTHER INFORMATION: FRT104 is one of a pair of FRT sequences
      (FRT4/FRT104) used in a DNA construct of the present invention

<400> SEQUENCE: 9
ctatactttc tagagaatag gaacttc                                       27

<210> SEQ ID NO 10
<211> LENGTH: 20
<212> TYPE: DNA
<213> ORGANISM: Artificial Sequence
<220> FEATURE:
<223> OTHER INFORMATION: FRT4W sequence reconstructed by recombination
      from a pair of FRT sequences (FRT4/FRT104)

<400> SEQUENCE: 10
ctatactttc tagagaatag                                               20

<210> SEQ ID NO 11
<211> LENGTH: 40
<212> TYPE: DNA
<213> ORGANISM: Artificial Sequence
<220> FEATURE:
<223> OTHER INFORMATION: Oligonucleotide synthesized to insert the
      FRT1-a sequence (including wild-type FRT sequence) into a plasmid

<400> SEQUENCE: 11
tcgacgaagt tcctatactt tctagagaat aggaacttcg                         40

<210> SEQ ID NO 12
<211> LENGTH: 40
<212> TYPE: DNA
<213> ORGANISM: Artificial Sequence
<220> FEATURE:
<223> OTHER INFORMATION: Oligonucleotide synthesized to insert the
      FRT1-b sequence (including wild-type FRT sequence) into a plasmid

<400> SEQUENCE: 12
aattcgaagt tcctattctc tagaaagtat aggaacttcg                         40

<210> SEQ ID NO 13
<211> LENGTH: 44
<212> TYPE: DNA
<213> ORGANISM: Artificial Sequence
<220> FEATURE:
<223> OTHER INFORMATION: Oligonucleotide synthesized to insert the
      FRT101-a sequence (including wild-type FRT sequence) into a
      plasmid

<400> SEQUENCE: 13
```

```
agcttgaagt tcctatactt tctagagaat aggaacttcg catg         44
```

<210> SEQ ID NO 14
<211> LENGTH: 36
<212> TYPE: DNA
<213> ORGANISM: Artificial Sequence
<220> FEATURE:
<223> OTHER INFORMATION: Oligonucleotide synthesized to insert the
      FRT101-b sequence (including wild-type FRT sequence) into a
      plasmid

<400> SEQUENCE: 14

```
cgaagttcct attctctaga aagtatagga acttca                  36
```

<210> SEQ ID NO 15
<211> LENGTH: 16
<212> TYPE: DNA
<213> ORGANISM: Artificial Sequence
<220> FEATURE:
<223> OTHER INFORMATION: Sequence of synthetic DNA used to prepare
      FRT2-a sequence

<400> SEQUENCE: 15

```
ctagagaata ggaacg                                        16
```

<210> SEQ ID NO 16
<211> LENGTH: 16
<212> TYPE: DNA
<213> ORGANISM: Artificial Sequence
<220> FEATURE:
<223> OTHER INFORMATION: Sequence of synthetic DNA used to prepare
      FRT2-b sequence

<400> SEQUENCE: 16

```
aattcgttcc tattct                                        16
```

<210> SEQ ID NO 17
<211> LENGTH: 18
<212> TYPE: DNA
<213> ORGANISM: Artificial Sequence
<220> FEATURE:
<223> OTHER INFORMATION: Sequence of synthetic DNA used to prepare
      FRT102-a sequence

<400> SEQUENCE: 17

```
agcttgttcc tatacttt                                      18
```

<210> SEQ ID NO 18
<211> LENGTH: 18
<212> TYPE: DNA
<213> ORGANISM: Artificial Sequence
<220> FEATURE:
<223> OTHER INFORMATION: Sequence of synthetic DNA used to prepare
      FRT102-b sequence

<400> SEQUENCE: 18

```
ctagaaagta taggaaca                                      18
```

<210> SEQ ID NO 19
<211> LENGTH: 14
<212> TYPE: DNA
<213> ORGANISM: Artificial Sequence
<220> FEATURE:
<223> OTHER INFORMATION: Sequence of synthetic DNA used to prepare
      FRT3-a sequence

<400> SEQUENCE: 19

```
ctagagaata ggag                                                    14

<210> SEQ ID NO 20
<211> LENGTH: 14
<212> TYPE: DNA
<213> ORGANISM: Artificial Sequence
<220> FEATURE:
<223> OTHER INFORMATION: Sequence of synthetic DNA used to prepare
      FRT3-b sequence

<400> SEQUENCE: 20
aattctccta ttct                                                    14

<210> SEQ ID NO 21
<211> LENGTH: 16
<212> TYPE: DNA
<213> ORGANISM: Artificial Sequence
<220> FEATURE:
<223> OTHER INFORMATION: Sequence of synthetic DNA used to prepare
      FRT103-a sequence

<400> SEQUENCE: 21
agctttccta tacttt                                                  16

<210> SEQ ID NO 22
<211> LENGTH: 16
<212> TYPE: DNA
<213> ORGANISM: Artificial Sequence
<220> FEATURE:
<223> OTHER INFORMATION: Sequence of synthetic DNA used to prepare
      FRT103-b sequence

<400> SEQUENCE: 22
ctagaaagta taggaa                                                  16

<210> SEQ ID NO 23
<211> LENGTH: 12
<212> TYPE: DNA
<213> ORGANISM: Artificial Sequence
<220> FEATURE:
<223> OTHER INFORMATION: Sequence of synthetic DNA used to prepare
      FRT4-a sequence

<400> SEQUENCE: 23
ctagagaata gg                                                      12

<210> SEQ ID NO 24
<211> LENGTH: 12
<212> TYPE: DNA
<213> ORGANISM: Artificial Sequence
<220> FEATURE:
<223> OTHER INFORMATION: Sequence of synthetic DNA used to prepare
      FRT4-b sequence

<400> SEQUENCE: 24
aattcctatt ct                                                      12

<210> SEQ ID NO 25
<211> LENGTH: 14
<212> TYPE: DNA
<213> ORGANISM: Artificial Sequence
<220> FEATURE:
<223> OTHER INFORMATION: Sequence of synthetic DNA used to prepare
      FRT104-a sequence

<400> SEQUENCE: 25
```
agcttctata cttt                                                   14

<210> SEQ ID NO 26
<211> LENGTH: 14
<212> TYPE: DNA
<213> ORGANISM: Artificial Sequence
<220> FEATURE:
<223> OTHER INFORMATION: Sequence of synthetic DNA used to prepare
      FRT104-b sequence

<400> SEQUENCE: 26
ctagaaagta taga                                                   14

<210> SEQ ID NO 27
<211> LENGTH: 29
<212> TYPE: DNA
<213> ORGANISM: Artificial Sequence
<220> FEATURE:
<223> OTHER INFORMATION: Oligonucleotide (GIN-1) synthesized to prepare
      a plasmid containing GIN11

<400> SEQUENCE: 27
tggatccgga atttcgacgg atcaataac                                   29

<210> SEQ ID NO 28
<211> LENGTH: 35
<212> TYPE: DNA
<213> ORGANISM: Artificial Sequence
<220> FEATURE:
<223> OTHER INFORMATION: Oligonucleotide (GIN-2) synthesized to prepare
      a plasmid containing GIN11

<400> SEQUENCE: 28
ttctgcagac tagatgcact catatcatta tgcac                            35

<210> SEQ ID NO 29
<211> LENGTH: 30
<212> TYPE: DNA
<213> ORGANISM: Artificial Sequence
<220> FEATURE:
<223> OTHER INFORMATION: Sequence of synthetic DNA to prepare a combined
      FRT3-b / FRT103-b sequence

<400> SEQUENCE: 29
aattctccta ttctctagaa agtataggaa                                  30

<210> SEQ ID NO 30
<211> LENGTH: 30
<212> TYPE: DNA
<213> ORGANISM: Artificial Sequence
<220> FEATURE:
<223> OTHER INFORMATION: Sequence of synthetic DNA to prepare a combined
      FRT103-a / FRT3-a sequence

<400> SEQUENCE: 30
agctttccta tactttctag agaataggag                                  30